United States Patent [19]

Kabalka

[11] 4,450,149

[45] May 22, 1984

[54] RADIOHALOGENATION METHOD

[75] Inventor: George W. Kabalka, Knoxville, Tenn.

[73] Assignee: Research Corporation, New York, N.Y.

[21] Appl. No.: 273,858

[22] Filed: Jun. 15, 1981

[51] Int. Cl.$^3$ .................... A61K 43/00; A61K 49/00
[52] U.S. Cl. ................. 424/1.1; 260/239.5; 424/9; 424/238
[58] Field of Search .............................. 424/1, 9, 238; 260/239.5

[56] References Cited

U.S. PATENT DOCUMENTS 4,184,037 1/1980 Wilkinson .............................. 536/7

OTHER PUBLICATIONS

Kabalka et al., J. Nucl. Med., 22:208–912, 1981.
De Lue et al., Synthesis, 2:114–116, 1976.
Kabalka et al., Chemical Abstracts, 96 (1982) Abstract #51928y.
Kabalka et al., Chemical Abstracts, 93 (1980) Abstract #132002g.
Kabalka et al., Chemical Abstracts, 95 (1981) Abstract #6665d.
Kabalka et al., Chemical Abstracts, 95 (1981) Abstract #203260u.
Gooch et al., Diss. Abstracts B, 42:1892, 1981.
Collins et al., J. Medicinal Chem., 20:1152–1159, 1977.

*Primary Examiner*—Christine M. Nucker
*Attorney, Agent, or Firm*—Scully, Scott, Murphy & Presser

[57] ABSTRACT

Organoborane compounds are halogenated by reacting an organoborane with iodinemonochloride, brominemono-chloride or a halide salt in the presence of a mild oxidizing agent.

29 Claims, No Drawings

RADIOHALOGENATION METHOD

BACKGROUND OF THE INVENTION

1. Field of the Invention

The present invention relates to a method of selectively introducing radioactive halogen atoms into organic molecules. More particularly, the present invention relates to a method of radioiodinating organic compounds of biological interest.

2. Description of the Prior Art

Radioisotopes, particularly iodine radioisotopes have been used extensively in nuclear medicine. The preferred utility of radioiodine in nuclear medicine is based on the relative accessability of a variety of useful iodine isotopes in comparison to other radiohalogen isotopes and the availability of relatively reliable techniques of incorporating radiohalogen atoms into organic compounds. For instance, recently $\omega$-iodofatty acids have been synthesized and evaluated as myocardial imaging agents. These studies have shown that certain of the halogenated acids are extracted by the myocardium as efficiently as oleic acid. Moreover, the myocardial $T_{\frac{1}{2}}$ of the $\omega$-iodofatty acids tends to be longer than the $T_{\frac{1}{2}}$ of the $\omega$-iodofatty acids because of the more remote positioning of the iodide in the $\omega$-derivatives.

Traditionally, the two most frequently employed isotopes found in radiopharmaceuticals are iodine-125 and technicium-99 m. Iodine-125 is by far the most useful radioisotope because of its convenient half life of 60 days. Technicium-99 m is, however, widely utilized even though it cannot radiolabel the variety of reagents which iodine-125 is capable of labeling. In recent years, with the discovery of computerized axial tomography, short-lived positron emitting nuclides such as carbon-11, bromine-75, iodine-121 and fluorine-18 have become very important. These reagents have relatively short half lives and thus are of limited utility. (For instance, brome-75 is a useful isotope but has a half life of only 98 minutes.)

Other recent reports of introducing various radionuclides into organic molecules have been reported. All of these techniques have the common feature that a radionuclide is introduced into an organic compound by an organoborane reactant. Kabalka, G. W. et al, J. Chem. Soc., Chem. Commun., 1979, 607; Kabalka, G. W., Syn. Commun., 1980, 10, 93 and Tang et al, J. Labelled Compd. Rad., 1979, XVI, 432 have demonstrated the introduction of carbon-14, carbon-13 and carbon-11 as labeled carbon monoxide or cyanide into organic molecules by reaction of the carbon monoxide or cyanide reactant with an organoborane. Organoboranes are known to react with a variety of different chemical reagents which include mineral acids such as hydrochloric acid under rather strenuous conditions of heating the organoborane at reflux in concentrated acid. Another reaction is the anti-Markovnikov addition of halogen to an olefinic bond by the reaction of the likes of bromine with an organoborane. However, this reaction proceeds rather slowly indicating difficulty in rupturing the carbon-boron bond of the organoborane reactant by $Cl_2$, $Br_2$ and the like.

Receptor-binding pharmaceutical compounds are of increasing interest in nuclear medical diagnoses. In this regard there has been a recent resurgence of interest in labeled estrogen derivatives because of their potential value as agents for visualization of estrogen receptor tissues. Many of the radiolabeled estrogens are prepared by using radioiodine isotopes because of their availability and proven utility. Unfortunately, many iodinated radiopharmaceuticals deiodinate rapidly in vivo. In order to counteract this problem, increased attempts have been made to develop procedures for plating iodine at less labile sites in molecules.

Traditionally, nearly all radiohalogenated materials have been made by substitution reactions, most of which are nucleophilic. However, some useful electrophilic procedures are known. For instance, Reese et al, U.S. Pat. No. 4,192,858, show the radioiodination of triiodothyronine ($T_3$) and Thyroxine($T_4$) by reaction of each of these materials with $Na^{125}I$ in the presence of chloramine-T. Newman, U.S. Pat. Nos. 4,195,073 and 4,223,002, shows the use of the chloramine-T reaction in radiolabeling alpha-fetoprotein with iodine-125. Still further, Sprinkle, U.S. Pat. Nos. 4,219,538, shows a process for radioiodinating human thyroid stimulating hormone with chloramine-T and sodium iodide-125. A major disadvantage of such substitution reactions is that because the reaction rates are dependent upon the concentration of reagents, the radiohalogenation reactions do not work well on small scales. Consequently, one encounters many difficulties in synthesizing desired radiohalogenated compounds such as the rate of formation, separation of radiolabeled product from the organic starting material and side reactions such as solvent attack on the organic starting material. Yields of only 2-10% are not uncommon in such conventional synthetic procedures. Still another drawback is that the availability of suitable organic starting materials for the radiolabeling reaction is often limited. In many cases the desired substitution reaction does not occur.

An extremely important consequence of the above mentioned reaction rate problem is that no-carrier-added reagents cannot be readily prepared by most radiolabeling techniques currently in use. No-carrier-added reagents are very important because the quantity of radiopharmaceutical compound can be kept below picogram levels. This minimizes body loads and aids in the differentiation of receptor-sites, and the like. In the light of the above discussed difficulties of preparing radiohalogenated compounds by standard substitution reactions, a need continues to exist for an improved technique of radiohalogenating organic compounds in high yields from reagents which are stable.

SUMMARY OF THE INVENTION

Accordingly, one object of the present invention is to provide a method of radiohalogenating organic compounds to the desired radiohalogenated product in high yields.

Another object of the present invention is to provide radiohalogenated organic compounds of improved stability.

Still another object of the present invention is to provide a method of readily radiohalogenating organic compounds difficult to radiohalogenate by conventional reaction methodology.

Yet another object of the invention is to provide a method of preparing no-carrier added radiohalogenated organic compounds.

Another object of the present invention is to provide a method of halogenating organic compounds at such a fast rate that compounds halogenated with such short life halogen isotopes as iodine-121 ($T_{\frac{1}{2}}=6.7$ hr), iodine-123 ($T_{\frac{1}{2}}=2.3$ hr), bromine-75 ($T_{\frac{1}{2}}=1.6$hr) and bromine- 77 (T½=2.3 days) can be prepared and effectively utilized.

Briefly, these objects and other objects of the present invention as hereinfter will become more readily apparent can be attained by a method of halogenating an organic compound by reacting a halide (radiohalide) salt with an organoborane compound in the presence of a mild oxidizing agent. In another aspect of the invention, an organic compound is halogenated by reacting an organoborane compound with iodine(radioiodine)-mono-chloride or bromine(radiobromine)monochloride with an organoborane.

DETAILED DESCRIPTION OF THE PREFERRED EMBODIMENTS

In one aspect of the halogenating reaction of the present invention, an organoborane compound is reacted with iodine monochloride or bromine monochloride. The reaction results in the cleavage of the carbon-boron bonds in the organoborane compound and the synthesis of an iodinated or brominated organic compound. The cleavage reaction occurs rapidly under relatively mild conditions. In the second aspect of the halogenation reaction, an organoborane compound is reacted with an iodide or bromide salt in the presence of a mild oxidizing agent resulting in cleavage of the carbon-boron bonds in the organoborane starting material and synthesis of an iodinated or brominated organic compound. Both processes can be performed with radiohalogen reactants.

In both aspects of the invention any organoborane compound which can be prepared may be reacted with the active halogenating agent to prepare the desired halogenated organic compound product. Organoboranes can be prepared by the well known methodology developed by H. C. Brown known as hydroboration in which an usaturated substrate such as an alkene, alkyne or the like is reacted with $BH_3$ in a stereospecific and regiospecific fashions i.e., the boron atom and a hydrogen atom adding to the site of unsaturation in a syn fashion with the boron attacking the least alkylated carbon atom of the site of unsaturation. Organoboranes can also be prepared by classical transmetallation reactions. This procedure is particularly useful in preparing aromatic boranes in which the boron atom of the borane is directly attached to the aromatic ring system. Organoborane compounds are unique among organometallic compounds in that a variety of functional groups may be present in the molecule because hydroboration at the site of unsaturation is faster than reduction of most functional groups. This feature is a particularly attractive aspect of the present invention as it relates to the preparation of radiohalide compounds because radiohalide compounds of medicinal, therapeutic or diagnostic utility, which can contain one or two to several different reactive functional groups, can be prepared by direct halogenation without concern of interfering side reactions involving additional functional groups in the organic starting material. Moreover, the boron atom of the organoborane is readily replaced by a variety of elements in a stereospecific manner with the element being added generally occupying the same region in space formerly occupied by the boron atom. In the case of halogenation reactions, however, halogen is usually introduced into the molecule with inversion of configuration at the carbon atom attacked by the halogenating agent. Examples of organic compounds which can be hydroborated include alkenes, alkynes cycloalkenes, cycloalkynes, unsaturated aldehydes, unsaturated carboxylic acids, unsaturated alcohols, unsaturated amines, unsaturated ketones, unsaturated nitro compounds and the like. Preferred organic compounds for hydroboration are those which give halogenated products of therapeutic, analytical or diagnostic interest such as unsaturated long chain fatty acids, preferably ω-unsaturated fatty acids, unsaturated steroidal compounds, unsaturated amines, unsaturated sugars, unsaturated prostaglandins, antigens, antibodies and the like. Radiohalogen labeled fatty acids are useful as myocardial imaging agent. Radiohalogen labeled steroidal compounds are potentially useful as breast tumor localizers. Other radiohalogenated organic materials include antigens such as $α$,-fetoprotein which are used in radioimmunoassay procedures, thyroxine and triiodothyronine. Radiohalogenated sugars are useful for brain imaging. Radiohalogenated amines such as spermidine and the like are potential imaging agents for the pancreas, while radiohaloganted alcohols are useful for liver imaging.

Several radiohalogenated compounds within the scope of the present invention include those of the formula:

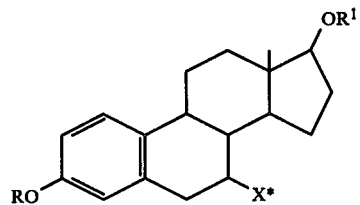

wherein $X^*$ is iodine-125, iodine-123 or bromine-75 and R and $R^1$ are independently hydrogen, methyl, ethyl or the like. A specific radiohalgenated steroidal product within the scope of the present invention is 17-(E-2-Iodovinyl)-1,3,5-estratrien-3,17 -diol-3 methylether. Radiohalogenated fatty acids within the scope of the present invention include those of the formula:

wherein $^*X$ is a radioactive iodine or bromine isotope and n is an integer of 8 to 18.

An outstanding feature of the present invention is that it provides a way by which no-carrier added radiochemical compounds can be prepared. Normally, in the preparation of radiohalogen substituted compounds by conventional techniques the radioactive halogen containing halogenating agent must be significantly diluted with nonradioactive halogenating agent in order to prepare a halogenated product in sufficient quantities for use. This is because in conventional halogenation processes, the rate of reaction is relatively shown and/or side reactions compete with the desired reaction. In order to obtain a sufficient quantity of halogenated product for work-up, the halogenating reagent is normally diluted with non-radioactive halogen containing reagent. This means that a major fraction of the halogenated product obtained is halogenated with non-radioactive halogen. During use of the halogenated compound synthesized, account must be made of the fact that the radiohalogenated compound prepared is substantially diluted with non-radioactive halogen containing material. For instance, when a carrier containing radiohalogenated compound is administered to an individual for the purpose desired, the quantity of compound administered must be large enough so that a sufficient quantity of radiohalogen containing compound is administered. This means that often undesirably large amounts of compound must be administered in order to administer the minimum amount of radiohalogen containing compound required for a given purpose. On the other hand, because of extremely rapid reaction kinetics in the present process and because few, if any, side reactions occur in the reaction of organoborane compounds with the present halogenating reactants, the halogenating reaction of the present invention can be conducted in extremely dilute systems. Because sufficient quantities of radiohalogen containing compound can be prepared by the present technique, the product radiohalogen compound does not have to be diluted by non-radiohalogen containing material. This means that the quantity of radiopharmaceutical prepared by the present technique can be kept to levels below picogram levels, thereby reducing the load or level of compound in a subject to minimum amounts. The fact that the present invention provides a way of administering no-carrier containing pharmaceuticals also means that with the appropriate radiopharmaceutical, differentiation of receptor sites and the like is aided. Indeed, no-carrier-added reagents are the goals set by most nuclear physicians.

The first aspect of the present invention can be represented by the following equations:

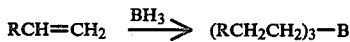

wherein X is iodine or bromine. An outstanding feature of the halogenation reaction is that it can be conducted under mild conditions giving relatively high yields of halogenated product. An indication of the relative ease at which the reaction occurs is the fact that the reaction can be conducted at a temperature ranging from $-100°$ C. to 25° C. Moreover, the pH of the reaction is not critical and can occur over a relatively wide range from about pH 1 to about pH 13. The reaction can be conducted in any solvent with the only requirement being that it should not be reactive with the starting reactants. Suitable solvents which can be used include cyclic ethers such as tetrahydrofuran, dioxane and the like; simple alcohols such as methyl alcohol, ethyl alcohol, propyl alcohol and the like; simple ethers such as diethyl ether, dipropyl ether and the like; polar solvents such as formamide and dimethylformamide and even water. When the halogenation reaction is conducted with ICl, the solution is preferably slightly basic. On the other hand, when the halogention reaction is conducted with BrCl, the reaction solution is preferably slightly acidic. Suitable bases include the alkali metal salts of weak acids such as sodium acetate, sodium propionate, sodium benzoate and the like. In generally depicting the reaction of an unsaturated organic compound with ICl or BrCl as shown above, consideration must be given to the fact that the hydroboration reaction is not limited to terminal olefinic groups but also olefinic sites located internally within linear, branched and cyclic hydrocarbon structures. The site of unsaturation can also be a triple bond located at terminal and internal positions in a molecule. Aromatic halides can also be prepared by known procedures via transmetallation reactions involving aromatic borane intermediates.

Examples of the halogenmonochloride reaction of the present invention are as follows:

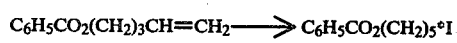

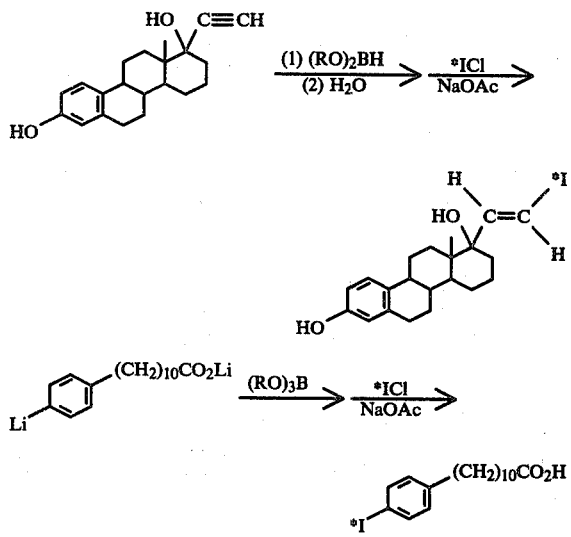

The second aspect of the present invention involves the reaction of an organoborane with bromide or iodide ion in the presence of a mild oxidizing agent, which can be shown generally as follows:

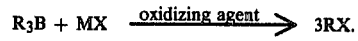

Suitable mild oxidizing agents which can be employed in this reaction include chloramine-T (N-chloro-p-toluenesulfonamide, sodium salt), chlorine gas, nitrite salts and the like. The reaction normally is conducted at temperatures ranging from as low as about $-100°$ C. to about 25° C., preferably from about $-78°$ C. to about 25° C. The reaction can be conducted in a variety of solvent media as disclosed above for the halogen monochloride reaction with the preferred solvents being water or a simple alcohol such as methanol, ethanol or the like. Any convenient iodide or bromide salt can be used in the reaction including ammonium, alkali metal and alkaline earth metal salts. Similar to the halogen monochloride reaction, the iodide or bromide salt reaction can be conducted over a wide pH range with the iodine reaction being somewhat facilitated by basic conditions while the bromine reaction is facilitated by acidic conditions. No harsh acids or bases are required to promote the reaction. To conduct the reaction an organoborane, either independently prepared or purchased, is placed in solution and then the halide salt dissolved in the solvent is added to the organoborane, preferably all at one time. Thereafter, the oxidizing agent is added to the solution either in a step-wise fashion or all at once depending on the rate of reaction. In the case of chloramine-T the oxidizer is normally added all at once and the reaction is increased by the addition of a mineral acid such as hydrochloric acid to the solution. Isolation of the halogenated product can then be readily achieved by separation of the organic layer containing the halogenated product from the remainder of the reaction mixture and then subsequent distillation, sublimation or crystallization of the product.

It seems to be clear that the reaction between halide salt and the mild oxidizing agent generates some type of electropositive iodine species in solution. For instance, the likes of chloramine-T presumably reacts with iodide or bromide ion to form halide monochloride or hydrated iodonium or hydrated bromonium ion which attacks the α-carbon atoms of the electron rich organoborane complex under mild reaction conditions.

Generally, it has been found that when a trialkylborane is prepared by the hydroboration of terminal alkenes, two of the three alkyl groups react instantly with the halogenating agent. In the case of trialkylboranes prepared from internal alkenes, one of the three alkyl groups reacts instantly. This type of reactivity parallels the reactions of organoboranes with iodine monochloride or bromine monochloride. The different reactivities of primary versus secondary alkyl groups can be utilized advantageously since a number of partially alkylated boranes are commonly used in organoborane syntheses. A complete discussion is beyond the scope of this application but reviews are available; however, the likes of dicyclohexylborane is readily prepared and it is a more selective hydroborating and reducing agent than borane ($BH_3$) itself. The following reaction demonstrates the utility of dicyclohexylborane as a hydroborating agent. As expected, the carboxylic acid functional group was not reduced and iodination proceeded normally.

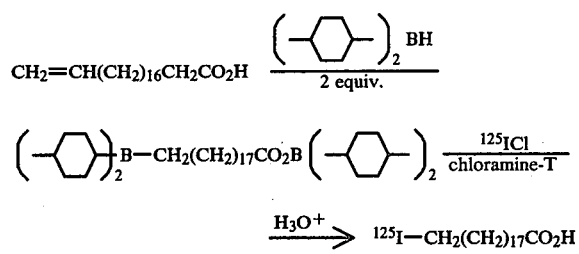

Arylorganoboranes can also be prepared, preferably by known transmetallation reactions and reacted with the halide ion mild oxidizing agent couple.

In both the halogen monochloride and halide salt reactions of the present invention the halogenating atom of the halogenating reagent can be radionuclide such as the important position-emitting nuclides, iodine-121 bromine-75, bromine-77. Also included are the medically important iodine-123, iodine-125, and iodine-131 nuclides which are gamma emitters.

Halogenation of Olefinic Bonds With Iodine Monochloride

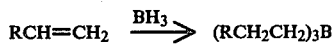

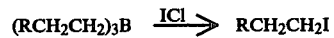

The data in Table 1 below show the results obtained from the iodination of trihexylborane with iodine monochloride in methanolic sodium acetate. The results indicate that the presence of excess iodine monochloride does not result in increased yields of product. However the presence of an additional equivalent of sodium acetate promotes the reaction. As shown by the data in the last column of the table, excesses of sodium acetate greater than one equivalent lead to diminished yield of product presumably because of secondary reactions of the product iodides.

TABLE 1

Conversion of Trihexylborane to n-Hexyl Iodide[a]
Yield (%)[c]

| Ratio of ICl/$R_3B$[a] | Ratio of NaOAc/$R_3B$ = 1:1 | Ratio of NaOAc/$R_3B$ = 2:1 | Ratio of NaOAc:$R_3B$ — 3:1 |
|---|---|---|---|
| 1 | 21 | 33 | 20[d] |
| 2 | 34 | 58 | 65 |
| 3 | 30 | 59 | 66 |

[a]Reaction of Trihexylborane (10 mmol) with ICl in THF (10 mL) at R.T. for 15 min. NaOAc added as 1.0 M solution in methanol.
[b]Ratios refer to ratio of mmoles of reagents.
[c]GLPC yields.
[d]In the presence of a large excess of sodium acetate, yields decrease.

Table 2 below shows a list of reactive olefinic group containing compounds only one of which does not also contain another functional group in the molecule, as well as the corresponding reaction product.

TABLE 2

Syntheses of Iodides

| Substrate | Product | Percent Yield (isolated)[b] |
|---|---|---|
| [structure] | [structure] | 88[b] |
| [structure] | [structure] | 97[b] |
| [structure] | [structure] | 75[b] |
| Cl~~~~= | Cl~~~~I | 82[b] |
| 1-Hexene[a] | 1-Iodohexane | 80[c] |
| [steroid structure] | [steroid structure] | |

The reaction of borane with olefinic group containing compounds is very rapid, however $BH_3$ also reduces carboxylic acids to alcohols. To overcome this problem, a number of reagents are known which hydroborate olefinic group containing compounds much more readily then they reduce carboxylic acids. These reagents include partially alkylated borane derivatives such as dicyclohexylborane (DCB), disioamylborane (DSB), and 9-borabicyclononane (9-BBN).

The versatility of the halogenation reaction with XCl can be demonstrated by the fact that it is useful for the iodination of ω-iodofatty acids as follows. In this reaction the hydroborating agent is dicyclohexylborane.

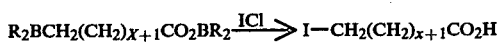

In the equation above X can have a value of 8 to 22, particularly the values of 8,13,16,19, and 22. The iodination reaction was conducted at 0° C. in the presence of sodium acetate. The details of the reaction are shown in Table 3 below as well as in the experimental section.

TABLE 3
Synthesis of Iodine-125 Labeled Fatty Acids Via Hydroboration-Iodination

| Starting Material[a] | Product | Radiochemical yield, %[b] |
|---|---|---|
| $CH_2=CH(CH_2)_8-CO_2H$ | $I-CH_2(CH_2)_9-CO_2H$ | 89 |
| $CH_2=CH(CH_2)_{13}CO_2H$ | $I-CH_2(CH_2)_{13}CO_2H$ | 89 |
| $CH_2=CH(CH_2)_{16}CO_2H$ | $I-CH_2(CH_2)_{17}CO_2H$ | 95 |
| $CH_2=CH(CH_2)_{19}CO_2H$ | $I-CH_2(CH_2)_{20}CO_2H$ | 90 |
| $CH_2=CH(CH_2)_8CH=CHCH_2CH_2CO_2CH_2CH_3$ | $I-CH_2(CH_2)_9CH=CHCH_2CH_2CO_2CH_2CH_3$ | 85[c] |

[a]The unsaturated materials were hydroborated with dicyclohexylborane and then reacted with iodine-125 monochloride (2 mCi/mole).
[b]Isolated yields.
[c]Chemical yield.

The hydroboration of olefin group containing compounds is known to proceed more rapidly for unhindered alkenes such as terminal vinyl groups than for more hindered unsaturated systems. This fact of differential reactivity can be taken advantage of in synthesizing certain types of compounds such as unsaturated ω-iodofatty acid esters which are useful in the synthesis of analogs of suicide inhibitors.

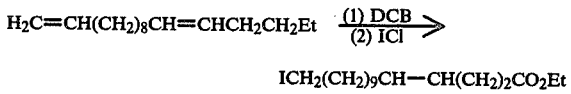

$$H_2C=CH(CH_2)_8CH=CHCH_2CH_2Et \xrightarrow[(2)\,ICl]{(1)\,DCB}$$

$$ICH_2(CH_2)_9CH-CH(CH_2)_2CO_2Et$$

The reaction of ICl with optically active diisopinocampheyl-2-butylborane demonstrates that in the bromination or iodination of many borane compounds, the reaction occurs with inversion of configuration at the carbon atom to which is attached the boron atom. The reaction can be shown as follows:

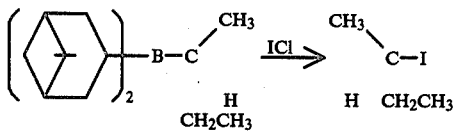

Experimental (Relevant to Data in Table 2)

Proton NMR spectra were recorded on a Varian Associates T-60 spectrometer. All chemical shifts are reported in parts per million downfield from TMS. The optical rotations were measured with a Rudolph Instruments MP7 Photoelectric Polarimeter using a sodium-D-lamp and a 10 mm cell.

All melting points and boiling points are uncorrected. The gas chromatography work was performed on a Varian Model 1700 dual column instrument with 6'×¼" 20% Carbowax C-20M on Chromosorb W and 6'×¼" 20% SE-30 on chromsorb W.

Commercially available samples (Aldrich) of 1-hexene, cyclohexene, safrole, and methyl 10-undecenoate were distilled from LiAlH or CaH₂ before use. 3-p-Tolylthio-2-methylpropene was prepared by the method described in J. Org. Chem. 1975, 40, 1776. (−)-α-Pinene was prepared from (−)-β-pinene (Crosby Chemical Co.) by the method described in J. Org. Chem., 35, 4266 (1970) and purified by spinning band distillation, []=−47.4° (92% optical purity.)

Hydroborations. General Procedure. The alkene (30 mmol) was dissolved in 5 ml of THF in a 100-ml, N₂-flushed, round bottom flask equipped with magnetic stirrer, septum inlet and reflux condenser. The solution was cooled to 0° C. and BH₃-THF (10 mmol, 5 ml of a 2 M solution) was added slowly via a syringe. The reaction mixture was heated to 50° C, stirred for one hour, and then cooled to room temperature.

Iodinations. General Procedure. Anhydrous methanol (1.0 ml) was added to the organoborane solution to destroy excess hydride. Methanolic sodium acetate (30 ml, 1. OM) was added, followed by the dropwise addition of iodine monochloride (20 mmol, 3.2 g). The mixture was stirred for 45 min. at room temperature and then poured into 100 ml of water. Sufficient aqueous sodium thiosulfate was added and then the mixture extracted with 3×30 ml of ether. The combined ether layers were dried over anhydrous MgSO₄ and the ether removed under reduced pressure. The products were isolated via column chromatography (alumina, mixed hexane eluent).

5-Benzoxy-1-pentene. Benzoyl chloride (0.2 mol, 23 ml) was added dropwise to a solution of 4penten-1-ol (0.2 mol, 20 ml) in pyridine and stirred overnight at room temperature. The reaction mixture was poured into 100 ml of water and the organic layer separated. The product mixture was washed, sequentially, with dilute HCl, saturated aqueous Na₂CO₃, and water. The organic layer was dried over anhydrous Na₂CO₃ and the product distilled: bp 90°-98° (1.0 mmHg); yield 26.9g, (71%); NMR (neat) δ 1.5 (broad m, 4, alkyl), 3.8 (t, 2, —OCH₂—), 4.6 (m, 2, =CH₂), 5.2 (m, 1, =CH—), 7.3 (m, 5, ArH).

5-Chloro-1-pentene. A solution of 4-penten-1 ol (0.15 mol, 15 ml) in 15 ml of ether and 15 ml of pyridine was added dropwise to a stirred solution of thionyl chloride (0.28 mol, 20 ml) in 15 ml of ether contained in a 100 ml flask fitted with a reflux condenser. The rate of addition was sufficient to maintain reflux. After addition of the alcohol, the ether was removed and additional thionyl chloride (0.07 mol., 5 ml) was added and the mixture stirred at 75° for 1.5 hr. The cooled mixture was poured into water and the organic layer separated. The aqueous layer was extracted with 2×30 ml of ether and the organic layers combined. The ether solution was dried over anhydrous Na₂CO₃, the ether removed under reduced pressure, and the product distilled: bp 45° (100 mmHg); yield 7.61 g (49%); NMR (CDCl₃) δ 2.1 (broad m, 4, alkyl), 3.5 (t, 2, —CH₂Cl), 5.0 (m, 2, =CH₂) 5.7 (m, 1, —CH=).

1-Iodohexane. 1-Hexene (30 mmol, 2.59 g) was hydroborated with BH₃-THE (10 mmol) and then iodinated with iodine monochloride (20 mmol). The yields were determined via GLPC analyses. The product exhibited spectral characteristics in accord with authentic samples.

1-Benzoxy-5-iodopentane. 5-Benzoxy-1-pentene (30 mmol, 5.7 g) was hydroborated with BH₃-THF (10 mmol) at 0° C. for 1 hr. Iodine monochloride (20 mmol, 1.0 ml) was added at room temperature; after 45 min, the product was isolated via chromatography (alumina): yield 5.63 g (88% based on ICl); bp 125° C./0.25 torr; m/e 318.1 (Calcd 318.2); IR (neat) 1705(C=O), 1205(C-I)cm$^{-1}$; NMR (neat) δ 1.7 (broad envelope, 6, alkyl), 3.0 (t, 2, —CH$_2$I), 4.2 (t, 2, —CH$_2$O—), 7.6 (m, 5, ArH).

3-p-Tolylthio-2-methyl-1-iodopropane. 3-p-Tolythio-2-methylpropene (30 mmol 5.35 g) was hydroborated with 10 mmol BH$_3$-THF at 0° C. Iodination was carried out at room temperature; after 45 minutes, the product was isolated via chromatography: yield 5.94 g (97%); bp 110/0.1 torr; m/e 306.2 amu (Calcd 306.2); IR (neat) 1195(C-I), 800(Ar-H)cm$^{-1}$; NMR (neat) δ 1.0 (d, 3H, —CH$_3$), 1.6 (m, 1, —CH—), 2.2 (s, 3, ArCH$_3$), 2.7 (m, 2, —CH$_2$I), 3.2 (d, 2, —SCH$_2$—), 7.0 (A'$_2$X'$_2$, 4, ArH).

3-(3,4-Methylenedioxyphenyl)-1-iodopropane. Safrole (30 mmol, 4.9 g) was hydroborated with 10 mmol of BH$_3$-THF at 0° C. for 1 hr. Iodination was carried out at room temperature. After 45 minutes, the product was isolated via chromatography: yield 4.32 g (75%); bp 105° C./0.08 torr; m/e 290.2 amu (Calcd 290.1); IR (neat) 1490(C=C), 1440(C=C), 1250(O-Ar), 1210(C-I), 1040(CH$_2$—O), 940(Ar-H), 800(Ar-H) cm$^{-1}$; NMR (neat) δ 2.0 (m, 2H, —CH$_2$—), 2.6 (t, 2, —CH$_2$I), 3.1 (t, 2, ArCH$_2$—), 5.8 (s, 2, —OCH$_2$O—), 6.6 (s, 3, ArH).

5-Chloro-1-iodopentane. 5-Chloro-1-pentene (30 mmol, 3.1 g) was hydroborated with 10 mmol BH$_3$-THF at 0° for 1 hr. Iodination was carried out at room temperature. After 45 minutes, the product was isolated via chromatography: yield 3.79 g (82%); bp 30-1/0.1 torr; m/e 232.3 amu (Calcd 232.5); IR (neat) 1300(C-Cl), 1200(C-I) cm$^{-1}$; NMR (CDCl$_3$) δ 1.8 (m, 6, —CH$_2$CH$_2$CH$_2$—), 3,2 (t, 2, —CH$_2$I), 3.6 (t, 2, —CH$_2$Cl).

Experimental (ω-Iodofatty acids Relevant to Table 3)

Reagents. Solvents were dried and stored under nitrogen via standard methods. BH$_3$.THF was prepared according to published procedures. Dicyclohexylborane was prepared via the hydroboration of cyclohexene with BH$_3$.THF (H. C. Brown et al., *J. Am. Chem. Soc.*, 89, 4530 (1967)). 11-Undecenoic acid, 11-bromoundecanoic acid and 8-bromooctanoic acid, (Aldrich Chem. Co.) were used as received. Iodine-125 monochloride (New England Nuclear), 50 Ci/mole was diluted to 6 m Ci/mole.

Microanalyses were performed commercially. Proton magnetic Resonance spectra were recorded on Varian T60A and EM 360A spectrometers. Mass spectral analyses were performed on a HP-5982 gc-mass spectrometer.

15-Hexadecenoic Acid. Prepared according to a published precedure.

18-Nonadecenoic Acid and 21-Docosenoic Acid. The magnesium chloride salt of the ω-bromoalkanoic acid (8-bromooctanoic acid or 11-bromoundecanoic acid) was prepared under positive nitrogen pressure by cooling a solution of 10 mmol of acid in 30-40 ml of anhydrous tetrahydrofuran (freshly distilled from lithium aluminum hydride) to −20° and adding 10 mmol methylmagnesium chloride (2.9 M solution in tetrahydrofuran) dropwise with stirring. Temperature and stirring were maintained for 0.5 hr. after addition was complete. To this cooled solution was added first, 2.0 ml of a 0.20 M solution of lithium copper tetrachloride in tetrahydrofuran and second, dropwise, a solution of Grignard reagent prepared from 2.33 g (10 mmol) 11-bromoundecene and 0.24 g (10 mmol) magnesium in 30 ml of sodium-dried diethyl ether. The reaction mixture was stirred for an additional 3 hr. at −20°, and then at ambient temperature overnight. The reaction mixture was worked- up by pouring it into a mixture of dilute sulfuric acid, ether and ice and extracting three times with ether. The combined ether extracts were extracted three times with 10% sodium bicarbonate solution, which resulted in a soapy emulsion. The combined emulsions were extracted with ether as best as possible, acidified and extracted three times with ether. The combined ether layers were washed with water and saturated sodium chloride solution, dried over anhydrous MgSO$_4$, and evaporated to dryness under reduced pressure to yield a white solid (crude yields of 80% were obtained). Recrystallization of the white solid from petroleum ether or petroleum ether-chloroform yielded pure compounds. The infrared spectra (IR) for these compounds were similar in that the principal peaks for each were observed at 1642 (w) (—CH=CH$_2$), 1710 (—CO$_2$H), 2860 and 2930 (—CH$_2$—)cm$^{-1}$ (CCl$_4$ solutions). PMR spectra were identical except for intensity of the —CH$_2$— absorption at 1.23 δ: PMR (CCl$_4$) δ:1.23 (s, 28H and 34H respectively, —CH$_2$—), 2.1 (m,4H,=CH—CH$_2$—and —CH$_2$—CO$_2$H), 4.7-6.03 (m,3H,—CH=CH$_2$), and 11.9 (s,1H,—CO$_2$H). Satisfactory elemental analyses were obtained. The melting point of 18-nonadecenoic acid is 59°-60° C. and the melting point of 21-docosenoic acid is 65°-67° C.

Preparation of ω-Iodofatty Acids. General Procedure. The appropriate alkenoic acid (100 mg), dissolved in 1 ml of THF, was added to two equivalents of dicyclohexylborane in THF at 0° C. After two hours, two equivalents of sodium acetate in methanol (1M soln.) was added followed by one equivalent of iodine-125 monochloride in methanol (1M soln.). After 0.5 hr at 25° C., the reaction mixture was poured into 10 ml of aqueous 2% acetic acid and 10 ml of pentane. Sodium thiosulfate was added to reduce excess iodine monochloride. The layers were separated and the aqueous layer extracted with 2×5 ml of pentane. The combined pentane layers were dried (anhyd. MgSO$_4$), the pentane removed under reduced pressure, and the product purified.

11-Iodoundecanoic. Prepared as described in general procedure. 10-Undecenoic acid (1.84 g, 10 mmol) was hydroborated with dicyclohexylborane (5 ml of 2M solution). The crude product was recrystallized from ligroin: ethyl aceate (90:10): yield 2.79 g (89%); mp 47°-50° C.; CI mass spectrum (CH$_4$) 313.4 (M+1, 100); NMR (CDCl$_3$) 1.2 δ (s, 14H, —CH$_2$—), 2.1 (m, 4H, —CH$_2$CO$_2$H and —CH$_2$CH$_2$I), 3.0 (t, 2H, —CH$_2$I), 11.9 (s, 1H, —CO$_2$H).

16-Iodohexadecanoic Acid. 15-Hexadecanoic acid (100 mg, 0.4 mmol) was hydroborated with dicyclohexylborane. The crude product was recrystallized from ligroin: ethyl acetate (90:10): yield 136 mg (89%); mp 71°-2° C.; mass spectrum m/e=382.6 (calcd. 382.4); NMR (CDCl$_3$) 1.2 δ (s, 24H, —CH$_2$—), 2.1 (m, 4H, —CH$_2$CO$_2$H and —CH$_2$CH$_2$I), 3.0 (t, 2H, —CH$_2$I), 11.9 (s, 1H, —CO$_2$H).

19-Iodononadecanoic Acid. 18-Nonadecenoic acid (100 mg, 0.34 mmol) was hydroborated with dicyclohexyl-borane. The crude product was flash chromatographed on 80-200 mesh silica gel with ligroin:ethyl acetate (80:20): yield 136 mg (95%); mp 70°-71.5° C.; mass spectrum m/e=424.5 (calcd. 424.5); NMR (CDCl$_3$) 1.2 δ (2, 30H, —CH$_2$—), 2.1 (m, 4H, —CH$_2$—CH$_2$—I), 3.0 (t, 2H, —CHI); 11.9 (s, 1H, —CO$_2$H).

22-Iododocosanoic Acid. 21-Docosenoic acid (100 mg, 0.3 mmol) was hydroborated with dicyclohexylborane. The crude product was flash chromatographed; yield 126 mg (90%); mp 71°-2° C.; mass spectrum m/e 466.5 (calcd. 466.5); NMR (CDCl$_3$), 1.2 (s, 36H, —CH$_2$—) (2.1 (m, —CH$_2$CO$_2$H and —CH$_2$CH$_2$I), 3.0 (t, 2H, —CH$_2$I), 11.9 (s, 1H, —CO$_2$E,uns/H/ ).

Ethyl 15-Iodo-4-pentadecenoate. 4,14-Pentadecadienoate (400 mg, 1.5 mmol) was hydroborated with dicyclohexylborane (1.5 mmol) at room temperature. The crude product was flash chromatographed on 80-200 mesh silica gel with ligroin:ethyl acetate (80:20): yield (85%); mass spectrum 394 (calcd. 394); NMR (CDCl$_3$) 1.2 δ (t, 3H, —CH$_3$), 1.3 (broad s, —CH$_2$—), 2.0 (broad s, 4H, —CH$_2$C=C and —CH$_2$CH$_2$I), 2.4 (s, 4H, —CH$_2$CH$_2$CO$_2$CH$_3$CH$_3$), 3.1 (t, 2H, —CH$_2$I), 4.0 (q, 2H, —CH$_2$CH$_3$), 5.3 (broad s, 2H, —CH=CH—).

Experimental (Inversion of Diisopinocampheyl-2-butylborane) R-(—)-2-Iodobutane A solution of diisopinocampheyl-2-butylborane (0.68 M) was prepared in diglyme. To 100 ml of this solution, iodine monochloride (50 ml, 2.8 M, diglyme solvent) and methanolic sodium acetate (100 ml, 1.4 M) were added simultaneously over a period of 15 minutes. [The additions, and the subsequent manipulations, were carried out in a darkened laboratory to prevent recemization of the product.] After the additions were complete, the mixture was stirred for 1 h at 25°. The mixture was added to 300 ml of ic water containing 0.3 g of sodium thiosulfate. The product was extracted with 6×50 ml of pentane; the combined pentane layers were extracted with 5×50 ml of ice water (to remove diglyme) and then dried over anhydrous magnesium sulfate. After removal of the solvent at 760 mm Hg, fractional distillation yielded pure R-(—)-2-iodobutane: bp 45° (60 mm Hg): [0]$_D$=27.95° (87% optical purity); NMR (CDCl$_3$) δ 0.95 (t, 3, —CH$_3$), 1.64 (q, 2, —CH$_2$—), 1.84 (d, 3, —CH$_3$—), 4.08 (sextuplet, 1, —CHI—).

Halogenation of Olefinic Bonds With Bromine Via Organoborane Intermediates

The alkenes shown in the first column of Table 4 are specific alkenes which, after hydroboration with BH$_3$.THF, were reacted with bromine monochloride and active bromine generated in situ from the reaction of bromide ion with chloramine-T. The results are also shown in the table. It is believed that the lower yields obtained for the bromide compounds prepared from the sec-alkene are due to steric constraints which limit the approach of the brominating species to the carbon attached to the boron atom.

TABLE 4

| Alkene | Product | % YIELD[a] | | |
|---|---|---|---|---|
| | | Br$_2$[b] | BrCl[c] | BrCl (in situ)[d] |
| ~~~~ | ~~~~Br | 69 | 85 | 85 |
| ✕ | ✕Br | 75 | 75 | 81 |

TABLE 4-continued

| Alkene | Product | % YIELD[a] | | |
|---|---|---|---|---|
| | | Br$_2$[b] | BrCl[c] | BrCl (in situ)[d] |
| ⋀ | ⋀Br | 70 | 62 | 92 |
| ◯ | ◯Br | 72 | 60 | 67 |
| ~~~⌃ | ~~~⌃Br | 5 | 5 | 5 |

[a]Isolated yields; in every case glpc yields are significantly higher. Yields are based on the brominating agent.
[b]Equimolar quantities of bromine and organoborane.
[c]Slight excess of freshly prepared bromine chloride used.
[d]Bromine chloride formed by in situ reaction of sodium bromide with chloramine-T.

The data in Table 5 show the bromination of functionally substituted alkenes after hydroboration with BH$_3$.THF, and in some instances dicyclohexylborane. The brominated products are shown as well as the yield of product. The yield data for the organoborane reactants prepared from BH$_3$.THF are based on the fact that only one of the three alkyl groups attached to the boron atom reacts. On the other hand, the yield data from organoboranes prepared from dicyclohexylborane show the bromination to be about twice as efficient as the bromination involving organoboranes prepared from BH$_3$.THF.

TABLE 5

| Alkene | Product | % Yield[a] | |
|---|---|---|---|
| | | Br$_2$[b] | BrCl[c] |
| ~(CH$_2$)$_8$CO$_2$CH$_3$ | Br~(CH$_2$)$_8$CO$_2$CH$_3$ | 96 | 99(68)[d] |
| ~~~O-Ph(C=O) | Br~~~O-Ph(C=O) | 99 | 91(70)[d] |
| ⋀S-Ph | Br⋀S-Ph | 91 | 61 |
| ~~⌬(O-O) | Br~~⌬(O-O) | 99 | 99(78)[d] |

[a]Isolated yields. Yields are based on the brominating agent.
[b]Equimolar amounts of bromine and organoborane.
[c]Bromine chloride formed in situ by reaction of sodium bormide and chloramine-T.
[d]The numbers in parenthesis refer to isolated yields based on starting alkene in reactions utilizing dicyclohexylborane as the hydroborating agent.

Experimental (The following is relevant to the data in Tables 4 and 5 above.)

Routine NMR spectra were recorded on a Varian Assoc. T-60 spectrometer. All chemical shifts are reported in parts per million downfield from Me$_4$Si. The Mass spectra were obtained using a HP-5982-A gc-mass spectrometer. The gas chromatography work was performed on a Varian Model 1700 instrument with a 6'×0.25" 20% Se-30 on Chromosorb W. Melting points are uncorrected.

Commercially available samples (Aldrich) of 1-hexene, cyclohexene, safrole, methyl 10-undecenoate, were distilled prior to use. 5-Benzoxy-1-pentene and 3-(p-tolylthio)-2-methylpropene were prepared according to published procedures.

Bromine Chloride Bromine chloride solutions (10 mmol) were prepared by adding sodium bromide (1.03 g, 10 mmol) to a solution of 70 ml of water and 35 ml of THF. Chlorine gas (15 mmoles, 0.67 ml of condensed $Cl_2$) was passed through the solution as a gas at room temperature. The solution was used immediately.

Hydroboration: General Procedure The alkene (15 mmol) was dissolved in 5 ml of THF in a 50 ml, $N_2$-flushed, round-bottomed flask equipped with a magnetic stirrer, septum inlet, and reflux condenser. The solution was cooled to 0° C. and $BH_3$-THF (5 mmol, 2.6 ml of a 1.91 M solution) was added via a syringe. The solution was stirred at 25° C. for 1 h.

Hydroboration: Dicyclohexylborane Procedure

Dicyclohexylborane [0.5 M] was prepared according to a published procedure. The alkene (5 mmole) was added to dicyclohexylborane [5 mmole] at 0° C. The mixture was stirred for 1 h while the temperature rose to 25° C.

Bromination: Molecular Bromine The organoborane (5 mmol) in THF was cooled to 0° C. Water (10 ml) was added and the reaction mixture shielded from light. Bromine (5 mmol) dissolved in THF (10 ml) at 0° C. was added to extract the product. The ether layer was washed with 2×30 ml of water, dried over anhydrous $MgSO_4$, and the solvent removed. The products were isolated by either column chromatography or preparative thick-layer chromatography.

Bromination: Bromine Chloride The organoborane (5 mmol) in THF was cooled to 0° C. Water (10 ml) was added and the reaction mixture shielded from light. The bromine chloride solution (5 mmol) was added at 0° C. and the reaction allowed to proceed for 30 minutes. The products were isolated as described in the bromine procedure.

Bromination: Bromine Chloride, in situ Sodium bromide (5.0 mmol, 0.515 g) in water (10 ml) was added to the organoborane (5.0 mmol) solution. The reaction mixture was cooled to 0° C. and shielded from light. Chloramine-T (2.28 g 10 mmol) in a mixture of THF (7.5 ml) and $H_2O$ (7.5 ml) was added all at once. An aqueous 10% HCl solution (10 ml) which had been saturated with NaCl was added dropwise to the mixture. The mixture was stirred for 15 min at 0° C. The mixture was extracted with ether (30 ml) and the products isolated as described in the bromine procedure. [The yields decrease if reaction times are longer than 15 min.]

1-Bromoalkanes The respective alkenes, 1-octene, 3,3-dimethyl-1-butene, 2-methyl-1-pentene, were hydroborated as described in the general procedure. Each trialkylorganoborane was brominated according to the three bromination procedures. The products were isolated by column chromatography on silica gel (pentane eluent). The products exhibited physical and spectral characteristics in accord with authentic samples. No effort was made to maximize the yields presented in Table I but the GLC yields were consistently higher than the isolated yields.

Methyl 11-Bromoundecanoate. (a) Methyl 10-undecenoate (15 mmol, 2.98 g) was hydroborated with $BH_3$.THF (5 mmol, at 0° C. for 1 hour. The brominations were carried out as described in the general procedures. The product was isolated via column chromatography; yield 4.17 g (99%) [96% via $Br_2$ reaction]; m.s. 199 [M-Br] (calcd. 278 and 280); IR (neat) 1740 $cm^{-1}$ (C=O); NMR ($CDCl_3$) 1.1–1.2 δ (broad singlet, 16H, alkane), 2.3 (t, 2H, —$CH_2$—$CO_2$—), 3.4 (t,2H, —$CH_2Br$); 3.58 (s, 3H, —$OCH_3$). (b) A similar reaction was carried out utilizing dicyclohexylborane (5 mmole) and the alkene (5 mmole). The yield of methyl 11-bromoundecanoate was 68%; 1.5 mmol of cyclohexyl bromide was also formed.

1-Benzoxy-5-bromopentane. [a] 5-Benzoxy-1-pentene (15 mmol, 2.85 g) was hydroborated with $BH_3$-THF (5 mmol) at 0° for 1 hr. The brominations were carried out as described in the general procedures. The product was isolated via column chromatography; yield 3.7 g (91%) [99% via the $Br_2$ reaction]; m.s. 269 and 271 (equal intensity) [M-1], [calcd. m/e=270 and 272]; NMR ($CDCl_3$) δ 1.7 (broad envelope, 6H, alkyl), 3.3 (t, 2H, —$CH_2$—O—), 7.3–7.9 (m, 5H, ArH). (b) A similar reaction was carried out utilizing dicyclohexylborane (5 mmol) and the alkene (5 mmol). The yield of 1-benzoxy-5-bromopentane was 70%; 1.4 mmol of cyclohexyl bromide was also formed.

3-p-Tolylthio-2-methyl-1-bromopropane. 3-p-Tolylthio-2-methylpropene (15 mmol, 2.67 g) was hydroborated with $BH_3$-THF (5 mmol) at 0°. The brominations were carried out as described in the general procedure. The product was isolated via chromatography; yield 2.67 g (61%); [90% via $Br_2$ reactions]; m.s. 257 and 259 [M-1] (calcd. 258 and 260); NMR ($CDCl_3$) δ 1.0 (d, 3H, —$CH_3$), 1.6 (m, 1H, —CH—), 2.2 (s, 2H, $ArCH_3$), 3.4 (m, 2H, —$CH_2Br$), 3.2 (d, 2H, —$SCH_2$), 7.0 ($A'_2X'_2$, 4H, ArH).

3-[3,4-Methylenedioxyphenyl]-1-bromopropane. (a) Safrole (15 mmol, 2.45 g) was hydroborated with $BH_3$-THF (5 mmol) at 0° for 1 hr. The brominations were carried out as described in the general procedure. The product was isolated via chromatography; yield 3.61 g (99%) [99% via $Br_2$ reaction]: m.s. m/e 242 and 244 (equal intensity) (calcd. 242 and 244). (The product contains 12% of the 2-bromo derivative); IR (neat) 1490(C=C), 1440(C=C), 1250(O-Ar), 1040($CH_2$—O),940(Ar-H), 800(Ar-H) $cm^{-1}$; NMR($CDCl_3$) δ 2.0 (m, 2H, —$CH_2$—), 2.8 (t, 2H, $ArH_2$—), 3.4 (t, 2H, —$CH_2Br$), 5.8 (s, 2H, —$OCH_2O$—), 6.6 (s, 3H, ArH). (b) A similar reaction was carried out utilizing dicyclohexylborane (5 mmol) and the alkene (5 mmol). The yield of 3-(3,4-methylenedioxyphenyl)-1-bromopropane was 78%; 1.1 mmole of cyclohexylbromide was also formed.

Hydroboration of Triple Bonds Compounds containing triple bonds can be hydroborated and then halogenated with ICl or BrCl to yield halogen bearing vinylic products. Table 6 below shows various triple bond containing reactants and the halogenated products formed by the reaction of the present invention.

TABLE 6

| Alkyne[a] | Product[b] | Isolated[c] Yield, % |
|---|---|---|
| HC≡$CH_2CH_2CH_2CH_3$ | ![I,H / C=C / H, $CH_2CH_2CH_2CH_3$] | 68(90)[d] |

TABLE 6-continued

| Alkyne[a] | Product[b] | Isolated[c] Yield, % |
|---|---|---|
| HC≡CCH₂CH₂CH₂Cl | (E)-ICH=CH-CH₂CH₂CH₂Cl | 73(90)[d] |
| HC≡C(CH₂)₈CO₂CH₃ | (E)-ICH=CH-(CH₂)₈CO₂CH₃ | 70 |
| | | 88 |

[a]The alkynes were hydroborated with catecholoborane and then hydrolyzed to the boronic acids. The boronic acids were reacted with iodine monochloride to yield product.
[b]Products were identified by IR, MNR, and mass spectral analyses.
[c]Yields based on boronic acid. See Experimental Section for details.
[d]Glpc yield is indicated in parenthesis.

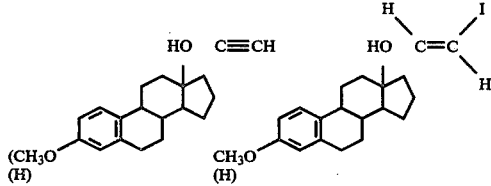

EXPERIMENTAL (Table 6)

(a) Preparation of the Boronic Acids:

The alkyne was placed in a dry, nitrogen flushed, round-bottomed flask. One equivalent of catecholborane was added. The mixture was heated to 70° C. for three hours. A large excess of water was added (slowly at first, due to evolution of hydrogen from unreacted catecholborane) and the mixture stirred overnight. The solid boronic acids were filtered and washed with copious amounts of water to remove catechol.

(b) Preparation of vinyl iodides:

The vinylboronic acid was dissolved in sufficient THF to yield a 0.5 M solution. The solution was cooled to 0° C. (or −78° C.) and two equivalents of sodium acetate were added (as a 1 M solution in Methanol). One equivalent of iodine monochloride was added (as a 1 M solution in methanol). After thirty minutes, the mixture was added to water and sufficient sodium thiosulfate was added to destroy excess iodine monochloride. The product was extracted into ether and isolated by column chromotography.

Products (E)-1-Iodohexene. 1-Hexyne (5.75 ml, 50 mmol) was hydroborated with catecholborane (5.38 ml, 50 mmol). The yield of 1-hexenylboronic acid was 5.85 g (92%); mp 99—100.5° C.; NMR (CDCl₃) δ 0.9 (m, 3H, —CH₃), 1.4 (m, 4H, —CH₂CH₂CH₃), 2.1 (m, 2H, —CH₂CH=C), 5.4 (d, 1H, C=CHB(OH)₂, J=17 Hz), 6.5 (d of triplets, 1H, —CH₂CH=C, J=7 Hz, J=17 Hz).

The 1-hexenylboronic acid (0.17 g, 1.33 mmol) was reacted with iodine monochloride (1.33 mmol, 1 M methanol soln.). The yield was 90% NMR (CCl₄) δ 0.9 (m, 3H, —CH₃), C=CHI), 1.4 (m, 4H, —CH₂CH₂CH₃), 2.1 (m, 2H, —CH₂CH=C), 5.85 (d, 1H, C=CHI), 6.25 (m, 1H, —CH₂—CHC).

(E)-1-Iodo-5-chloro-1-pentene. %-Chloro-1-pentyne (8.7 g, 85 mmol) was reacted with catecholborane. The yield of boronic acid was 9.11 g (73%); m/e 148.2 (calcd. 148.4); NMR (CD₃COCD₃) 1.4–2.2 δ (m, 4H, —CH₂CH₂CH₂Cl), 3.2 (t, 2H, Cl—CH₂—), 5.4 (d, 1H, —CH=CHB(OH)₂, J=17 Hz) 6.5 (m, 1H, —CH=CH-B(OH)₂).

The boronic acid (5.92 g, 40 mmol) was reacted with iodine monochloride to yield 7.0 g (76%); m/e 230.2 (58%) and 232.2 (17%) [calcd. 230.5 and 232.5]; NMR (CCl₄) 2.0 δ(m, 4H, Cl—CH₂CH₂CH₂—), 3.45 (t, 2H, ClCH₂), 6.0 (d, 1H, —C=CHI, J=15 Hz), 6.2 (d of triplets, 1H, —CH₂CH=CHI).

Methyl (E)-11-Iodo-10-undecenoate. Methyl 10-undecynoate was prepared via the reaction of 10-undecynoic acid (Farchan) with diazomethane. The ester (1.6 g, 8 mmole) was hydroborated with catecholborane. The yield of the boronic acid was 1.7 g (87%); mp 48.5–50; mass spectrum, 316.9 (calcd. m/e 316.1); NMR (CDCl₃) 1.3 δ(broad s, 12H, alkane), 2.35 (broad envelope, 4H, —CH₂CH=,—CH₂CO₂), 3.6 (s, 3H, —OCH₃), 5.38 (d, 1H, —C=CHB, J=17 Hz), 6.4 (m, 1H, —CH=CHB).

The boronic acid (198 mg, 0.81 mmol) was reacted with iodine monochloride to yield 183 mg of the product iodide. The product was isolated by column chromatography using neutralaluminaand pentane as eluent; mass spectrum, 197 [M-127] (calcd. 324.2); NMR (CDCl₃) 1.35 δ(broad s, 12H, aliphatic), 2.35 envelope, 4H, —CH₂C= and —CH₂CO₂CH₃), 3.6 s, 3H, —OCH₃), 5.85 (doublet, 1H, —CH=CHI, J=14 Hz), 6.4 (m, 1H, —CHI).

17-(E-2-Iodovinyl)-1,3,5-estratrien-3,17β-diol-3 methyl ether. Mestranol, IIIa, (3.1 g, 10 mmol), Sigma Chemical Co., was placed in a dry, nitrogen-flushed 50 ml flask containing catecholborane (3.2 ml, 30 mmol), Aldrich Chem. Co. The mixture was heated to 70° C. for 2 hr. Water (25 ml) was added to the solution carefully at first, to destroy the excess hydride and to convert the vinylboronic ester intermediate to the vinylboronic acid. After stirring overnight, the boronic acid was filtered, washed with 5×50 ml of cold water, and dried: yield 3.64 g (98%); mp 148°–150° C.; mass spectrum, 312.6 [M-44,—B(OH)₂] (calcd. m/e 356.6); NMR(DMSO-d₆) δ 0.9 (s, 3H, —CH₃), 1.0–2.8 (broad envelope, 15 H, steroid nucleus), 3.6 (s, 3H, —OCH₃), 5.4 (d, 1H, C=CHB(OH)₂, J=17.5 Hz) 6.5–7.2 (complex multiplet, 4H, ArH and —CH=CHB(OH)₂).

The vinylboronic acid, (0.364 g, 1 mmole) was placed in a dry, nitrogen-flushed, 25 ml flask containing 5 ml of THF. The solution was cooled to −40° C; sodium acetate in methanol was added (2 ml of a 1 M soln) followed by the dropwise addition of iodine-125 monochloride in methanol (1 ml of a 1 M soln; activity=6 mCi/mole), New England Nuclear Corp. The mixture was allowed to warm to room temperature and added to a mixture of ether and water. The excess iodine monochloride was reduced by the addition of small amounts of sodium thiosulfate. The ether layer was separated and the solvent removed. The product was isolated by preparative TLC (silica gel) using petroleum ether:methanol:ethyl acetate (200:25:25); R=0.5; mass spectrum, 439 (M+1, calcd. m/e 438); NMR (CCl₄) δ 0.9 (s, 3H, —OCH₃), 1.1–2.8 (broad envelope, 15H, steroid nucleus), 3.6 (s, 3H, —OCH₃), 6.2 (d, 1H, C—CHI), 6.4–7.2 (complex multiplet, 4H, ArH and —CH—CHI);activity=6.0 mCi/mole; radiochemical yield=88%.

17-(E-2-Iodovinyl)- Δ¹,³,⁵-estratrien-3,17β-diol. Ethynyl estradiol (300 mg, 1.01 mmol), Sigma Chemical Co., was placed in a dry, nitrogen-flushed 50 ml flask containing catecholborane (0.492 ml, 4.56 mmol). The mixture was heated to 70° C. for 2 hours and then water (1.5 ml) was carefully added to destroy excess hydride and hydrolyze the vinylboronic ester intermediate to the vinylboronic acid. After stirring overnight at room temperature the mixture was transferred to a separatory funnel and the product extracted into ether. The ether was removed and the vinylboronic acid product was purified by TLC (silica gel) using petroleum ether:methanol:ethyl acetate (250:35:35), Rf=0.25; mass spectrum, 298.6 [M-44, —B(OH)$_2$] (calcd. m/e 342.6); NMR (DMSO-d$_6$) δ 0.9 (s, 3H, —CH$_3$), 1.2–2.8 broad multiplet, steroid nucleus) 5.4 (d, 1H, —CH=CHB(OH)$_2$, J=17 Hz), 6.5 to 7.2 (complex multiplet, 4H, ArH and —CH=CHB(OH)$_2$); yield 173 mg (50%).

The vinylboronic acid product (100 mg, 0.28 mmol) was placed in a dry, nitrogen-flushed, 5 ml flask containing 1 ml of THF. The solution was cooled to −40° C.; sodium acetate in methanol was added (0.5 ml of a 1 M soln) followed by the dropwise addition of iodine-125 monochloride in methanol (activity=6 m Ci/mole), New England Nuclear Corp. The mixture was allowed to warm to room temperature and added to a mixture of ether and water. The excess iodine monochloride was reduced by the addition of small amounts of sodium thiosulfate. The ether layer was separated, dried, and the solvent removed. The product was isolated by preparative TLC (silica gel) using petroleum ether:methanol:ethyl acetate (200:35:35), Rf=0.2: mass spectrum, m/e 424 (calcd. 424); NMR (CDCl$_3$) 0.9 (s, 3H, —CH$_3$), 1.1–2.9 (broad envelope, steroid nucleus), 6.6 (d, 1H, —CH=CHI), 6.8–7.2 (complex multiplet, ArH and —CH—CHI); radiochemical yield=64%.

Halogenation of Olefinic Bonds With a Halide Sale and a Mild Oxidizing Agent

The reaction of an organoborane with a halide salt in the presence of a mild oxidizing agent can be shown as follows:

$$R_3B + X^- \xrightarrow{\text{mild oxidizing agent}} 3\,RX$$

Specific examples of this reaction are shown in Table 7, the first column of which shows the initial alkene reactant used to prepare an organoborane by reaction of the alkene with BH$_3$.THF and the middle column of which shows the specific iodinated product obtained by reaction of the organoborane with 2 equivalents of iodine-127(NaI)+2 equivalents of chloramine-T.

TABLE 7

| Alkene | Product | Yield[a] |
|---|---|---|
| CH$_2$=CH(CH$_2$)$_3$CH$_3$ | I—CH$_2$(CH$_2$)$_4$CH$_3$ | 99 |
| (cyclohexene) | (cyclohexyl iodide) | 99[b] |
| benzoate of pent-4-en-1-ol | benzoate of 5-iodopentyl | 94 |
| 3-(p-tolylthio)-2-methylpropene | 3-(p-tolylthio)-2-methyl-3-iodopropane 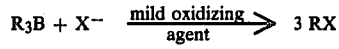 | 99 |

TABLE 7-continued

| Alkene | Product | Yield[a] |
|---|---|---|
| safrole (methylenedioxyallylbenzene) | iodinated safrole | 78 |
| CH$_2$=CH(CH$_2$)$_8$CO$_2$CH$_3$ | I—CH$_2$(CH$_2$)$_9$CO$_2$CH$_3$ | 94 |
| CH$_2$=CH(CH$_2$)$_{16}$CO$_2$H | I—CH$_2$(CH$_2$)$_{17}$CO$_2$H | 89[c] |
| CH$_2$=CH(CH$_2$)$_{19}$CO$_2$H | I—CH$_2$(CH$_2$)$_{20}$CO$_2$H | 91[c] |

[a] Isolated yields based on iodide except for hexyl iodide and cyclohexyl iodide which are GLC yields.
[b] One equivalent of sodium iodide utilized.
[c] Alkene reacted with two equivalents of dicyclohexylborane and one equivalent of sodium iodide.

Experimental (Relevant to Table 7)

Materials and Methods

Chemical Reagents. Commercially available samples (Aldrich) of 1-hexene, cyclohexene, safrole and methyl 10-undecenoate were used as received. Tetrahydrofuran (THF) was distilled prior to use. 5-Benzoxy-1-pentene, 3-(p-tolythio)-2-methylpropene, 18-nonadecenoic acid and 21-docosenoic acid were prepared according to published procedures.

Iodine-125 in 0.1M NaOH (17 Ci/mg) New England Nuclear)) was diluted to 3 mCi/mole before use. One synthesis of methyl 11-iodoundecanoate was carried out using no carrier added sodium iodide (17 Ci/mg).

Chemical and Radiochemical Purity Analyses. The chemical and radiochemical purity of the products were determined by thin layer chromatography using silica gel plates (250μ with fluorescent indicator, Fisher Scientific Co.). The unlabeled products were applied adjacent to the radiolabeled products. In all systems, > 95% of the radioactivity was associated with a single spot having an R$_f$ value identical to that of the unlabeled material. Radiochemical yields were obtained by isolation of the product via column chromatography (silica gel). Radioactivity determinations were made on a Packard 5220 Auto-Gamma Scintillation Spectrometer. The unlabeled compounds were characterized by their infrared, nuclear magnetic resonance, and mass spectra. Routine NMR spectra were recorded on a Varian Associates T-60 spectrometer. All chemical shifts were reported in parts per million downfield from Me$_4$Si. All melting points and boiling points are uncorrected. The mass spectra were obtained using a HP-5982-A gc-mass spectrometer with a HP-5934 data package.

Hydroboration: General Procedure. The alkene (3 mmol) was dissolved in 1 ml of THF in a 10 ml, N$_2$-flushed, round-bottomed flask equipped with a magnetic stirrer and septum inlet. The solution was cooled to 0° C. and BH$_3$-THF (1 mmol, 0.5 ml of a 2M solution) was added via a syringe. The solution was stirred at 25° C. for 1 hour.

Hydroborations: Dicyclohexylborane Procedure. The alkene (50 mg) was dissolved in 0.5–1.0 ml of THF and then two equivalents of dicyclohexylborane were added at 0° C. The solution was stirred at 25° C. for 1 hour.

Iodinations: General Procedure. Methanolic sodium acetate (two equivalents), aqueous sodium iodide (2 equivalents), and chloramine-T (two equivalents) were added sequentially to the organoborane solution. [For reactions involving dicyclohexylborane derivatives only one equivalent of sodium iodide was used.] The mixture was stirred for 1 minute at 25° C. and then quenched by adding aqueous sodium thiosulfate (1.0 M) and HCl (1.0 N). The reaction mixture was poured into a mixture of 20 mL of water and 10 ml of pentane. The aqueous layer was washed with 2×5 ml of pentane. The combined pentane layers were washed with 5-10 ml of saturated aqueous sodium chloride solution. The pentane was removed by evaporation and the product isolated by chromatography (silica gel, ethyl acetate/hexane as eluent).

1-Iodohexane. 1-Hexane was hydroborated with $BH_3$-THF and then iodinated as described in the general procedure. The product exhibited physical characteristics in accord with an authentic sample.

Iodocyclohexane. Cyclohexane was hydroborated with $BH_3$-THF and then reacted with iodide as described in the general procedure. The product exhibited physical characteristics in accord with an authentic sample.

1-Benzoxy-5-iodopentane. 5-Benzoxy-1-pentene (3 mmol, 570 mg) was hydroborated with $BH_3$-THF (1 mmol) at 0° C. at 1 hour. The resultant organoborane was iodinated as outlined in the general procedure. The product was isolated via column chromatography (silica gel, mixed hexanes eluent): yield 600 mg (94%). The product exhibited physical charcteristics in accord with an authentic sample.

3-(p-Tolylthio)-2-methyl-1-iodoprpane. 3-(p-Tolylthio)-2-methylpropene (3 mmol, 535 mg) was hydroborated with $BH_3$-THF (1 mmol) at 0° C. for 1 hour. The resultant organoborane was iodinated as described in the general procedure. The product was isolated via column chromatography: yield 610 mg (100%); the product exhibited physical characteristics in accord with an authentic sample.

3-[3,4-(Methylenedioxy)phenyl]-1-iodopropane. Safrole (3 mmol, 490 mg) was hydroborated with $BH_3$-THF (1 mmol) at 0° C. for 1 hour. The organoborane was iodinated as described in the general procedure. The product was isolated via column chromotography: yield 452 mg (78%); the product exhibited physical characteristics in accord with an authentic sample.

Methyl 11-Iodoundecanoate. Methyl 10-undecenoate (3 mmol, 595 mg) was hydroborated with $BH_3$-THF (1 mmol) at 0° C. for 1 hour. The iodination was carried out as described in the general procedure. The product was isolated via column chromotography; yield 614 mg (94%); m.s. 199 [M-I] (calcd. m/e=326); IR (neat) 1740 $cm^{-1}$ (C=O); NMR($CDCl_3$) 1.1-1.2 δ (broad singlet, 16H, alkane), 2.25 (t, 2H, —$CH_2$—$CO_2$—), 3.28 (t, 2H, —$CH_2I$), 3.58 (s, 3H, —$OCH_3$).

Methyl 11-Iodoundecanoate (No-Carrier Added). Methyl 10-undecenoate (0.22 ml, 1 mmole) was hydroborated with dicyclohexylborane (1 mmole, 1M). One micromole of the organoborane was diluted to 100 microliters using THF; sodium acetate (1 μmole) was added to this solution. Sodium iodide-125 (2.7 p-mole, 2.0 mCi) was added to the mixture followed by aqueous chloramine-T (1 μmole, 10 μl of a 0.1M solution). The product was identified by TLC on silica gel (ligroin/ethyl acetate (90:10), $R_f$=0.7). Radiochemical yield=55%.

19-Iodononadecanoic acid. 18-Nonadecenoic acid (100 mg, 0.34 mmol) was hydroborated with dicylohexylborane (0.7 mmol) at 0° C. The organoborane was iodinated with sodium aceate (0.7 mmol), sodium iodide (0.35 mmol), and chloramine-T (0.7 mmol). The product was isolated by column chromatography on silica gel (10% ethyl acetate:hexane):yield 129 mg (89%); m/e=424.5 (calcd 424.5); NMR ($CDCl_3$) 1.2 δ (s, 30H, alkane), 2.1 (m, 4H, —$CH_2CO_2H$—$CH_2I$), 3.0 (t, 2H, —$CH_2I$), 11.9 (s, 1H, —$CO_2H$).

22-Iodododocosanoic acid. 21-Docosenoic acid (55mg. 0.16 mmol) was hydroborated with dicyclohexylborane (0.32 mmol) at 0° C. The organoborane was iodinated with a mixture of sodium aceate (0.32 mmol), sodium iodide (0.16 mmol), and chloramine-T (0.32 mmol). The product was isolated by a column chromatography on silica gel (10% ethyl acetate:hexane):yield 68 mg (91%); mp 71°-2° C.; m/e 466.5 (calcd 466.5); NMR ($CDCl_3$), 1.2 δ (s, 36H, alkane), 2.1 (m, 4H, —$CH_2$—$CO_2H$ and —$CH_2CH_2I$), 3.0 (t, 2H, —$CH_2I$, 11.9 (s, 1H, —$CO_2H$).

Iodobenzene. Triphenylborane was prepared according to a published procedure. The triphenylborane (247 mg, 1.02 mmol) was placed in a 5 ml, dry, nitrogen-flushed flask containing 1.5 ml of THF. Sodium acetate, sodium iodide, and chloramine-T(1.02 mmol) were added at room temperature. The yield of iodobenzene (100%) was determined via gas chromatography. [Yield based on the migration of one phenyl group per organoborane molecule.]

Tissue Distribution Study The radioiodinated 19-$^{125}I$-iodononadecanoic acid was evaluated in female Spraque-Dawley rats weighing 250-350 g. The rats were given food and water ad libidum. For the tissue distribution study, approximately 25 μCi of the fatty acid in a physiological formulation (EtOH/Tween 80/0.9% saline: 2.5 ml/0.65 ml/22 ml) was administered intravenously to ether anesthetized rats. Five animals were sacrificed at 5 min post injection. Representative 50-100 mg samples of heart, liver, lung, blood, and muscle were removed and cleaned of fat and connective tissue. Samples were counted in an auto-gamma scintillation counter and values corrected for radioactive decay, counting efficiency and background. The resulting tissue concentration values were normalized to a per kilogram body weight and are reported in % kg dose/g. as shown in Table 8.

TABLE 8[a]

| Compound | Heart | Liver | Blood | Lung | Muscle |
|---|---|---|---|---|---|
| Prepared Via Present Method | 0.71 ± 0.01[b] | 0.47 ± 0.03 | 0.13 ± 0.00 | 0.24 ± 0.02 | 0.14 ± 0.00 |
| 19-$^{125}I$—iodononadecanoic acid reported in J. Nucl. Med., 22:0000, 1981 | 0.88 ± 0.23 | 0.53 ± 0.02 | 0.15 ± 0.01 | 0.28 ± 0.04 | 0.19 ± 0.00 |

[a]Average of 5 rats (standard deviation)
[b]Value reported as % kg dose/g

Having now described the invention, it will be apparent to one of ordinary skill in the art that many changes and modifications can be made thereto without departing from the spirit or scope of the invention as set forth herein.

I claim:

1. A method of radiohalogenating an organic compound, comprising:

reacting a radiohalide salt with an organoborane compound derived from said organic compound in the presence of a mild oxidizing agent.

2. A method of halogenating an organic compound, comprising:
reacting a halide salt with an organoborane compound derived from said organic compound in the presence of a mild oxidizing agent.

3. The method of claim 1 or 2, wherein said mild oxidizing agent is selected from the group consisting of chlorine, nitrite ion and N-chloro-p-toluenesulfonamide.

4. The method of claim 1, wherein said radiohalide salt is a salt formed with a component selected from the group consisting of an alkaline earth metal, alkali metal or ammonium iodide-125, iodide-123, bromide-75, and bromide-77 salt.

5. The method of claim 1, wherein said organoborane is the borane addition product of said organic compound which is selected from the group consisting of an ω-unsaturated fatty acid, thyroxine, triiodothyronine, α,-fetoprotein, an unsaturated steroidal compound, an unsaturated alcohol, an unsaturated amine, an unsaturated sugar and an unsaturated prostaglandin.

6. The method of claim 1 or 2, wherein said reaction is conducted at a temperature of $-100°$ C. to $25°$ C.

7. The method of claim 1 and 2, wherein said reaction is conducted in the presence of a solvent selected from the group consisting of water, an aliphatic alcohol, dimethylformamide, tetrahydrofuran and dioxane.

8. The method of claim 1 or 2, wherein said reaction is conducted in water at a pH of 1 to 13.

9. The method of claim 2, wherein said halide salt is a salt of a component selected from the group consisting of nonradioactive alkaline earth metal, alkali metal or ammonium iodide and bromide salt.

10. The method of claim 2, wherein said organoborane is the borane addition compound of said organic compound which contains an olefinic group or a triple bond.

11. A method of radiohalogenating an organic compound, comprising:
reacting radioiodinomonochloride or radiobrominemonochloride with an organoborane derived from said organic compound.

12. A method of halogenating an organic compound, comprising:
reacting iodinemonochloride or brominemonochloride with an organoborane derived from said organic compound.

13. The method of claim 11 or 12, wherein said reaction is conducted at a temperature of $-100°$ C. to $25°$ C.

14. The method of claim 11 or 12, wherein said radiohalogenmonochloride reactant is $^{123}$ICl, $^{125}$ICL, $^{75}$BrCl or $^{77}$BrCl.

15. The method of claim 11, wherein said organoborane is the borane addition product of said organic compound which is selected from the group consisting of an ωunsaturated fatty acid, thyroxine, triiodothyronine, α-feto- protein, an unsaturated steroidal compound, an unsaturated alcohol, an unsaturated amine, an unsaturated sugar and an unsaturated prostaglandin.

16. The method of claim 11 or 12, wherein said reaction is conducted in water at a pH of 1 to 13.

17. The method of claim 11 or 12, wherein said reaction is conducted in the presence of a solvent selected from the group consisting of water, an aliphatic alcohol, dimethylformamide, tetrahydrofuran and dioxane.

18. A radiopharmaceutical of the formula:

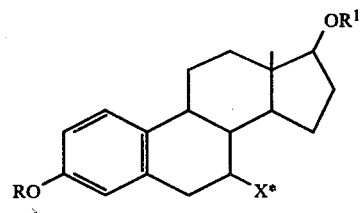

wherein X* is iodine-125, or bromine-75 and R and R' independently are hydrogen, methyl or ethyl.

19. The compound of claim 18, wherein R is methyl, R' is hydrogen and X* is iodine-125.

20. The compound of claim 18, wherein R and R' are hydrogen and X* is iodine -125.

21. No-carrier-added radiotherapeutic compounds wherein the radionuclide of said radiotherapeutic compounds is selected from the group consisting of iodine-123, iodine-125, bromine-75 and bromine-77.

22. No-carrier added radiodiagnostic compounds wherein the radionuclide is selected form the group consisting of iodine-123, iodine-125, bromine-77 and bromine-75.

23. The compound of claim 22, wherein said no-carrier added radiotherapeutic compound is selected from the group consisting of an ω-iodofatty acid, a radioiodide or radiobromide substituted steroidal compound, a radioiodide or radiobromide substituted amine, a radioiodide or radiobromide substituted sugar and a radioiodide or radiobromide substituted alcohol.

24. The compound of claim 23, wherein said no-carrier added radiotherapeutic compound is a radioiodide or radiobromide substituted prostaglandin.

25. A radiopharmaceutical of the formula:

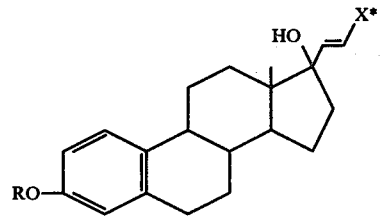

wherein X* is a radiohalogen atom and R is hydrogen or alkyl.

26. The compound of claim 25, wherein R is methyl.

27. The compound of claim 25, wherein said radiohalogn atom is iodine-125, iodine-123, iodine-121, bromine-77, or bromine-75.

28. A method of claim 6 wherein said reaction is conducted at a temperature of from about $-78°$ C. to about $25°$ C.

29. A method of claim 13 wherein said reaction is conducted at a temperature of from about $-78°$ C. to about $25°$ C.

* * * * *